United States Patent [19]

Warwel et al.

[11] Patent Number: 5,344,946
[45] Date of Patent: Sep. 6, 1994

[54] PROCESS FOR THE PREPARATION OF VICINAL DIOLS AND/OR EPOXIDES

[75] Inventors: Siegfried Warwel; Mark R. Klaas, both of Aachen; Michael Sojka, Gelnhausen, all of Fed. Rep. of Germany

[73] Assignee: Solvay Interox GmbH, Hollriegelskreith, Fed. Rep. of Germany

[21] Appl. No.: 65,461

[22] Filed: May 20, 1993

Related U.S. Application Data

[63] Continuation-in-part of Ser. No. 864,496, Apr. 7, 1992, abandoned.

[30] Foreign Application Priority Data

Apr. 9, 1991 [DE] Fed. Rep. of Germany ....... 4111506

[51] Int. Cl.$^5$ ................ C07D 301/12; C07D 303/04; C07C 27/16; C07C 31/20
[52] U.S. Cl. .................... 549/531; 554/138; 568/821; 568/833; 568/860
[58] Field of Search ............... 549/531; 568/860, 821, 568/833; 554/138

[56] References Cited

U.S. PATENT DOCUMENTS

| | | | |
|---|---|---|---|
| 3,113,951 | 12/1963 | Williams | 549/531 |
| 3,518,285 | 6/1970 | Fenton et al. | 260/348.5 |
| 3,646,130 | 2/1972 | Parshall | 260/533 C |
| 3,778,451 | 12/1973 | Poite | 549/531 |
| 3,953,480 | 4/1976 | Delavarenne | 549/531 |
| 4,303,586 | 12/1981 | Schirmann et al. | 549/531 |
| 4,418,203 | 11/1983 | Kim | 549/531 |
| 4,973,718 | 11/1990 | Buchler et al. | 549/531 |
| 5,036,154 | 7/1991 | Au | 549/531 |

FOREIGN PATENT DOCUMENTS

| | | | |
|---|---|---|---|
| 9262 | 4/1980 | European Pat. Off. | 549/531 |
| 0308791 | 3/1989 | European Pat. Off. | |
| 3902357 | 8/1990 | Fed. Rep. of Germany. | |
| 132877 | 6/1987 | Japan | 549/531 |

OTHER PUBLICATIONS

Chemical Abstracts, vol. 116, Abstract No. 58690E (1992) World Patent Index–Week 6800 JP–44–020 449 (1969).

*Primary Examiner*—Joseph E. Evans
*Attorney, Agent, or Firm*—McCormick, Paulding & Huber

[57] ABSTRACT

The present invention provides a process for the preparation of vicinal diols and/or epoxides by the oxidation of olefinically-unsaturated compounds with the use of an inorganic heptavalent rhenium compound as catalyst and of hydrogen peroxide as oxidation agent, wherein the reaction is carried out in a solvent selected from the group consisting of organic phosphoric acid esters and ethers with a boiling point above 50° C. under atmospheric conditions.

24 Claims, No Drawings

PROCESS FOR THE PREPARATION OF VICINAL DIOLS AND/OR EPOXIDES

This is a continuation-in-part of co-pending application Ser. No. 864,486 filed on Apr. 7, 1992, abandoned.

The present invention is concerned with a process for the preparation of vicinal diols and/or epoxides by the oxidation of olefinically-unsaturated compounds with inorganic heptavalent rhenium compounds as catalyst and hydrogen peroxide as oxidising agent.

Vicinal diols and epoxides are compounds of industrial importance. They find use in the fields of washing and cleaning agents, as well as of cosmetics, and serve as synthetic material plasticisers and as starting materials for the production of synthetic materials, especially in polyurethane chemistry.

As a rule, epoxides are obtained technically (with the exception of ethylene oxide) by reacting olefins and functionalised olefines with percarboxylic acids or hydroperoxides. Vicinal diols are prepared from the corresponding epoxides by saponification.

Transition metal-catalysed oxidations of carbon—carbon double bonds by means of hydrogen peroxide are known (cf. for example R. S. Sheldon, J. K. Kochi, "Metal-catalyzed oxidations of organic compounds", pub. Academic Press, N.Y. 1981). The classical process in this connection thereby uses the system $OsO_4/H_2O_2$ (Milas' reagent) which converts olefines via osmate esters into cis-glycols according to the following equation:

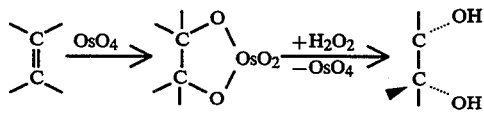

However, because of the high toxicity of osmium tetroxide and for cost reasons, the process has not been used industrially.

In DE-OS 39 02 357 A1, there are described the epoxidations and hydroxylations of olefines by means of catalysis by methyl rhenium trioxide ($CH_3ReO_3$) and other organo-metallic compounds of rhenium.

The catalysts are thereby prepared by the reaction of rhenium heptoxide with main group organo-metallic compounds. This is disadvantageous since the main group organo-metallic compounds are expensive and some of them are highly toxic compounds. The methyl rhenium trioxide preferably employed as catalyst is, according to Herrmann et al. (Angew. Chem., 100, 420/1988), prepared by the reaction of rhenium heptoxide with tetramethyl tin according to the following equation:

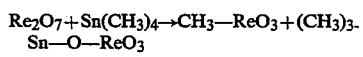

The tetramethyl tin used is very toxic and 50% of the rhenium heptoxide employed is converted into the catalytically inactive stannyl ester. A separation of the catalyst and reuse thereof is also not possible, the rhenium compounds being fixed on to polymeric carriers, which further complicates the preparation of the catalyst and makes it more expensive. Furthermore, the activity of the catalyst is clearly reduced in comparison with monomeric rhenium compounds, for example methyl rhenium trioxide.

U.S. Pat. No. 3,518,285 discloses a process for the oxidation of olefins to an oxidised compound selected from the class consisting of epoxides and ketones with the same total number of carbon atoms, which process comprises contacting an olefinic hydrocarbon containing 3 to 20 carbon atoms with a rhenium compound selected from the group consisting of rhenium oxide and alkali metal, alkaline earth metal and ammonium perrhenates in a liquid reaction medium which contains a solvent which is inert under the oxidation conditions and 3 to 90% by weight of hydrogen peroxide, the reaction medium being under a pressure which suffices in order to keep the medium as a liquid and at a temperature of from −50° C. to 150° C. which suffices in order to oxidise the olefin to the oxidised compound. As examples of appropriate solvents, there are mentioned aromatic hydrocarbons, aliphatic hydrocarbons, halogenated hydrocarbons, carboxylic acid esters and nitriles. Furthermore, the water produced during the reaction is removed from the reaction medium in order to maintain the oxidation of the olefin. However, this process has serious disadvantages insofar as only very low yields of diols and epoxides are obtained from the olefinically-unsaturated compounds. On the other hand, the formation of further oxidised secondary products, such as ketones and carboxylic acids, or of polymeric condensation products is observed.

Thus, it is an object of the present invention to provide a process for the preparation of diols and/or epoxides by the oxidation of olefinically-unsaturated compounds in which the disadvantages of the prior art are at least partly overcome.

In particular, a process is to be provided which gives epoxides and vicinal diols in high yield with the use of non-toxic and reusable catalysts.

Thus, according to the present invention, there is provided a process for the preparation of vicinal diols and/or epoxides by the oxidation of olefinically-unsaturated compounds with the use of an inorganic heptavalent rhenium compound as catalyst and of hydrogen peroxide as oxidation agent, wherein the reaction is carried out in a solvent selected from the group consisting of organic phosphoric acid esters and saturated ethers, excluding cyclic three-ring ethers (epoxides), with a boiling point above 50° C. under atmospheric conditions.

Having regard to the prior art, the very good suitability of inorganic heptavalent rhenium compounds as catalysts for the oxidation of olefines with the use of particular solvents is very surprising. Thus, in DE-OS 39 02 357, in which the use of organo-metallic rhenium compounds is described, it is pointed out that the use of rhenium oxides, for example rhenium heptoxide, or perrhenates, such as sodium perrhenate, as catalysts for the oxidation of olefins was unsuccessful.

The use of appropriate solvents is important for the process according to the present invention. We have ascertained that organic phosphoric acid esters and saturated ethers, excluding cyclic three-ring ethers (epoxides), with a boiling point above 50° C. under atmospheric conditions give good yields. On the other hand, we have found that the solvents disclosed in U.S. Pat. No. 3,518,285, for example aromatic hydrocarbons, aliphatic hydrocarbons, halogenated hydrocarbons, esters and nitriles, do not give acceptable yields.

If organic phosphoric acid esters are used as solvents, then phosphoric acid trialkyl esters are preferred in which each alkyl radical can contain up to 10 carbon atoms and in which the alkyl radicals can be the same or different. Phosphoric acid trialkyl esters in which each alkyl radical contains 2 to 8 carbon atoms are especially preferred, triethyl phosphate and tri-n-butyl phosphate being most preferred.

When using ethers with a boiling point of more than 50° C. under atmospheric conditions, cyclic and acyclic ethers with several and especially with 2 to 4 ether groups are preferred. Preferred examples of such compounds include 1,4-dioxane, dimethoxyethane (glyme) and diethyleneglycol dimethyl ether (diglyme). The boiling points of 1,4-dioxane, glyme and diglyme are 101° C., 84° C. and 160° C., respectively. However, there can also be used high boiling point ethers with only one ether group for example di-n-butyl ether (b.p. 140° C.) and dibenzyl ether (b.p. 300° C.).

As starting compounds for the process according to the present invention, there are used olefinically-unsaturated compounds, i.e. cyclic or acyclic compounds with one or more carbon-carbon double bonds, i.e. monoolefins, diolefins or polyenes. In the case of acyclic olefins, the carbon-carbon double bond can be not only terminal but also within the molecule. These compounds can be optionally substituted with one or more functional groups, for example a hydroxyl group, a carboxylic acid group, a carboxylic acid ester group or an aryl radical and especially a phenyl radical. Examples of appropriate open-chained, unsubstituted olefins include octenes, such as 1-octene, decenes, such as 5-decene, dodecenes, such as 1-dodecene and 6-dodecene, tetradecenes, such as 1-tetradecene and 7-tetradecene, as well as hexadecenes and octadecenes. Examples of cyclic olefins include cyclohexene, cycloheptene, cyclooctene and cyclodecene. Examples of substituted olefins include open-chained unsaturated carboxylic acids, such as 10-undecenoic acid, as well as the alkyl and aryl esters thereof, such as methyl 10-undecenoate.

Inorganic heptavalent rhenium compounds are used as catalysts. Examples of such compounds include rhenium heptoxide and perrhenates of the general formulae $M(ReO_4)$ and $M'(ReO_4)_2$, in which M is an alkali metal or ammonium and M' is an alkaline earth metal. The rhenium compounds can thereby also be added to the reaction mixture in the form of compounds with a lower oxidation stage, including metallic rhenium and rhenium carbonyl complexes. Such compounds are also catalytically effective since, due to the hydrogen peroxide present in the reaction mixture, they are oxidised to catalytically-active heptavalent rhenium compounds (see, for example, U.S. Pat. No. 3,518,285).

The process according to the present invention is carried out at an acidic pH value and preferably at a pH value of less than 3. It is especially preferred to use a pH value of from 0 to 2, a pH value of about 1 having proved to be the most favourable. In the case of the use of rhenium heptoxide as catalyst, perhaps depending upon the solvent used, without further measures there is obtained an optimum pH value of about 1. If a perrhenate is used as catalyst, the pH value of the reaction mixture is favourably adjusted by the addition of a strong inorganic or organic acid to give a pH value of less than 3 and preferably of about 1. The inorganic or organic acids appropriate for this purpose should not be oxidisable by hydrogen peroxide under the reaction conditions. Examples of inorganic acids include sulphuric acid, phosphoric acid and perchloric acid, perchloric acid being preferred. Examples of organic acids include alkyl and aryl sulphonic acids, such as toluenesulphonic acid.

For the process according to the present invention, the catalyst is preferably used in a concentration of from 0.2 to 5 mol %, referred to an oxidisable carbon—carbon double bond of the olefinically-unsaturated starting compound. Especially preferred is the use of the catalyst in a concentration of from 0.8 to 1.2 mol %, referred to one oxidisable carbon—carbon double bond of the olefinically-unsaturated starting compound.

The catalysts used for the process according to the present invention are especially characterised in that, after separation of the reaction product from the reaction mixture, for example by filtration, they remain in the reaction medium and can again be used in this form as catalyst solution without the catalytic activity decreasing or without any working up or activation of the catalyst having to be carried out. In this way, a multiple reuse of the catalyst is possible.

In the process according to the present invention, hydrogen peroxide is used in a concentration of from 30 to 85% and is preferably used as a 60% aqueous solution. The molar ratio of hydrogen peroxide to an oxidisable carbon-carbon double bond of the olefinically-unsaturated starting compound is preferably from 1:1 to 4:1 and especially preferably of about 1.2:1. However, it is also possible to use the olefin in excess.

The temperature used for the process according to the present invention is, as a rule, from ambient temperature to 100° C. and preferably of from 70° to 90° C. However, in special cases, temperatures below 20° C. can also be employed.

As reaction products in the case of the oxidation of olefinically-unsaturated compounds, there are preponderantly obtained vicinal diols. However, by means of the choice of lower reaction temperatures and higher catalyst concentrations, those conditions can also be adjusted under which epoxides are the main product of the reaction.

The carrying out of the reaction preferably takes place in such a manner that the compound to be oxidised is added to the solvent and then the catalyst is added thereto, followed by the dropwise addition of hydrogen peroxide. This can take place at ambient temperature (as in the following Examples) so that the reaction mixture is only heated up to the reaction temperature after the addition of the hydrogen peroxide. After completion of the reaction, the reaction mixture is preferably cooled to 0° C. and mixed with a mild reducing agent, for example sodium sulphite, in aqueous solution. The reaction products can be removed from the resulting mixture for example by extraction with an organic solvent or, if they are insoluble, by filtration. However, the same results are obtained when, even before the addition of hydrogen peroxide, the mixture is heated to the reaction temperature.

The following Examples are given for the purpose of illustrating the present invention.

EXAMPLE 1

Oxidation of 1-octene 0.05 mol (5.6 g) of 1-octene is dissolved in 20 ml triethyl phosphate and 0.5 mmol (0.24 g) rhenium heptoxide is added thereto. 0.06 mol (3.4 g, 60%) hydrogen peroxide is slowly added thereto at ambient temperature, while stirring. After 16 hours at 90° C., the reaction mixture is cooled to 0° C. and mixed with about 30 ml of a saturated aqueous solution of sodium sulphite. The solution is repeatedly extracted with diethyl ether and the combined organic extracts are evaporated on a rotary evaporator.

The product mixture remaining behind is subjected to a GC and GC/MS analysis. On the basis of authentic comparison compounds, it is ascertained that, besides unreacted educt, it contains octane-1,2-diol and 1-octane oxide. By means of the addition of a GC standard (ethyl oenanthate), having regard to correction factors previously determined by means of pure compounds, there are quantitatively determined the amounts of reaction products formed. In this and in the following Examples, the yield is, in each case, referred to the olefin used.

Yield of octane-1,2-diol: 37% of theory, referred to the olefin

Yield of 1-octene oxide: 11% of theory, referred to the olefin.

In the case of the use of tri-n-butyl phosphate as solvent and with otherwise the same manner of carrying out the process, there are obtained 41% of diol and 9% of epoxide. With the use of triisooctyl phosphate as solvent, there are obtained 27% of diol and 8% of epoxide.

EXAMPLE 2

Oxidation of 7-tetradecene 0.03 mol (5.9 g) of 7-tetradecene is dissolved in 20 ml triethyl phosphate and 0.3 mmol (0.14 g) rhenium heptoxide added thereto 0.036 mol (2.0 g, 60%) hydrogen peroxide is slowly added thereto, while stirring. Subsequently, the reaction mixture is stirred for 16 hours at 90° C.

Working up can take place according to two procedures:

a) The reaction mixture is mixed with double the volume of ethanol (about 60 ml) and subsequently with about 20 ml of aqueous sodium sulphite solution. The solution is repeatedly extracted with diethyl ether and the combined organic extracts are evaporated on a rotary evaporator.

For the purpose of converting the diols formed into the trimethylsilyl ethers thereof, the remaining product mixture is silylated in the usual way and subsequently subjected to a GC and GC/MS analysis. On the basis of authentic comparative substances, it is ascertained that, besides unreacted educt, the product contains tetradecane-7,8-diol in the form of the trimethylsilyl ester. By means of the addition of a GC standard (diethyl phthalate), having regard to correction factors previously determined by means of pure substances, the amounts of the trimethylsilyl ethers formed are determined quantitatively. The yield of silylated tetradecane-7,8-diol is 67% of theory, referred to the olefin.

b) The reaction mixture is cooled to 0° C. and mixed with about 20 ml of aqueous sodium sulphite solution, a white solid material thereby precipitating out which is separated off by filtration.

By means of elementary analysis and comparison of the GC/MS spectrum with an authentic sample, the solid material is identified as being tetradecane-7,8-diol; m.p. 70°-73° C., of an authentic sample 69°-70° C. The yield of tetradecane-7,8-diol is 4.1 g (59% of theory, referred to the olefin).

EXAMPLE 3

Oxidation of 1-tetradecene 0.03 mol (5.9 g) 1-tetradecene is dissolved in 20 ml 1,4-dioxane and 0.3 mmol (0.14 g) rhenium heptoxide is added thereto. 0.036 mol (2.0 g, 60%) hydrogen peroxide is slowly added dropwise thereto, while stirring. Subsequently, the reaction mixture is stirred for 16 hours at 90° C., then cooled to 0° C. and mixed with about 20 ml of aqueous sodium sulphite solution. A solid material thereby precipitates out which is separated off by filtration.

By means of elementary analysis and comparison of the GC/MS spectrum with a sample which has been prepared by the hydroxylation of 1-tetradecene with performic acid, the solid material is identified as being tetradecane-1,2-diol; m.p. 59°-61° C., m.p. of an authentic sample 62°-64° C.. The yield of tetradecane 1,2-diol is 4.2 g (61% of theory, referred to the olefin).

EXAMPLE 4

Oxidation of 7-tetradecene 0.03 mol (5.9 g) 7-tetradecene is dissolved in 20 ml 1,4-dioxane and 0.3 mmol (0.14 g) rhenium heptoxide is added thereto. 0.036 mol (2.0 g, 60%) hydrogen peroxide is slowly added dropwise thereto, while stirring. Subsequently, the reaction mixture is stirred for 16 hours at 90° C., then cooled to 0° C. and mixed with about 20 ml of aqueous sodium sulphite solution, a white solid material thereby precipitating out which is separated off by filtration. The yield of tetradecane-7,8-diol is 4.9 g (71% of theory, referred to the olefin).

EXAMPLE 4a

If working is carried out as in Example 4 but using 0.20 g dirhenium decacarbonyl instead of rhenium heptoxide, there are obtained 4.6 g of diol (67% of theory, referred to the olefin).

EXAMPLE 5

Oxidation of cyclohexene 0.05 mol (4.1 g) cyclohexene is dissolved in 20 ml triethyl phosphate and 0.5 mmol (0.24 g) rhenium heptoxide is added thereto. 0.06 mol (3.4 g, 60%) hydrogen peroxide is slowly added dropwise thereto, while stirring. Subsequently, the reaction mixture is stirred for 16 hours at 70° C., thereafter cooled to 0° C. and mixed with about 20 ml of aqueous saturated sodium sulphite solution. The reaction mixture is repeatedly extracted with diethyl ether and the reaction product is separated off by fractional distillation.

The product is identified by comparison of the GC/MS spectrum with that of an authentic sample and by elementary analysis. The yield of cyclohexane-1,2-diol is 4.3 g (74% of theory, referred to the olefin).

EXAMPLE 6

Oxidation of further olefins

The following further olefins are reacted under conditions analogous to Example 3:

| olefin | reaction product | yield in % of theory referred to the olefin |
|---|---|---|
| a) 1-dodecene | dodecane-1,2-diol | 62 |

-continued

| olefin | reaction product | yield in % of theory referred to the olefin |
|---|---|---|
| b) 1-hexadecene | hexadecane-1,2-diol | 80 |
| c) 1-octadecene | octadecane-1,2-diol | 77 |
| d) 4-octene | octane-4,5-diol | 60 |
| e) 5-decene | decane-5,6-diol | 52 |
| f) 6-dodecene | dodecane-6,7-diol | 54 |
| g) 9-octadecene | octadecane-9,10-diol | 80 |
| h) cycloheptene | cycloheptane-1,2-diol | 35 |
| i) cyclooctene | cyclooctane-1,2-diol | 52 |
| j) cyclododecene | cyclododecane-1,2-diol | 68 |

EXAMPLE 7

Oxidation of 9-octadecene with catalyst recycling a) 0.03 mol (7.6 g) 9-octadecene is dissolved in 20 ml 1,4-dioxane and 0.3 mmol (0.14 g) rhenium heptoxide is added thereto. 0.036 mol (2.0 g, 60%) hydrogen peroxide is slowly added dropwise thereto, while stirring. Subsequently, the reaction mixture is stirred for 16 hours at 90° C. and thereafter cooled to 0° C. A white solid material precipitates out which is separated off by filtration.

By means of elementary analysis and comparison of the GC/MS spectrum with that of an authentic sample, the solid material is identified as being octadecane-9,10-diol, the yield of octadecane-9,10-diol being 4.4 g (51% of theory, referred to the olefin).

b) The filtrate from Example 7a) is returned to the reaction vessel and 0.02 mol (7.5 g) 9-octadecene, as well as 5 ml 1,4-dioxane, again added thereto. A further 0.036 mol (2.0 g, 60%) hydrogen peroxide is added dropwise thereto and the reaction mixture is again stirred for 16 hours at 90° C., cooled and the product isolated by filtration. The yield of octadecane-9,1diol is 6.7 g (78% of theory, referred to the olefin).

c) The filtrate from Example 7b) is returned to the reaction vessel and 0.03 mol (7.6 g) 9-octadecene, as well as 5 ml 1,4-dioxane, again added thereto. A further 0.036 mol (2.0 g, 60%) hydrogen peroxide is added dropwise thereto and the reaction mixture is again stirred for 16 hours at 90° C., cooled and the product isolated by filtration. The yield of octadecane-9,10-diol is 7.0 g (81% of theory, referred to the olefin).

d) The filtrate from Example 7c) is returned to the reaction vessel and 0.03 mol (7.6 g) 9-octadecene, as well as 5 ml 1,4-dioxane, again added thereto. A further 0.036 mol (2.0 g, 60%) hydrogen peroxide is added dropwise thereto and the reaction mixture is again stirred for 16 hours at 90° C., cooled and the product isolated by filtration. The yield of octadecene-9,10-diol is 6.1 g (71% of theory, referred to the olefin).

e) The filtrate from Example 7d) is returned to the reaction vessel and 0.03 mol (7.6 g) 9-octadecene, as well as 5 ml 1,4-dioxane, again added thereto. A further 0.036 mol (2.0 g, 60%) hydrogen peroxide is added dropwise thereto and the reaction mixture is again stirred for 16 hours at 90° C., cooled and the product isolated by filtration. The yield of octadecane-9,10-diol is 5.7 g (66% of theory, referred to the olefin).

f) The filtrate from Example 7e) is returned to the reaction vessel and 0.03 mol (7.6 g) 9-octadecene, as well as 5 ml 1,4-dioxane, again added thereto. A further 0.036 mol (2.0 g, 60%) hydrogen peroxide is added dropwise thereto and the reaction mixture is again stirred for 16 hours at 90° C., cooled and the product isolated by filtration. The yield of octadecane-9,10-diol is 7.8 g (91% of theory, referred to the olefin).

In the case of using the catalyst six times, the total yield of octadecane-9,10-diol is 73% of theory, referred to the total amount of olefin used.

EXAMPLE 8

Oxidation of 7-tetradecene 0.03 mol (5.9 g) 7-tetradecene is dissolved in 20 ml 1,4-dioxane and 0.3 mmol (0.09 g) potassium perrhenate is added thereto. Such an amount of a 60% aqueous solution of perchloric acid is added thereto that the pH value decreases to 1. 0.036 mol (2.0 g, 60%) hydrogen peroxide is slowly added dropwise thereto, while stirring. Subsequently, the reaction mixture is stirred for 16 hours at 90° C. Thereafter, it is cooled to 0° C. and mixed with about 20 ml of an aqueous saturated solution of sodium sulphite. A white solid material thereby precipitates out which is separated off by filtration. The yield of tetradecane-7,8-diol is 3.9 g (56% of theory, referred to the olefin).

EXAMPLE 9

Oxidation of methyl 10-undecenoate 0.03 mol (6.0 g) methyl 10-undecenoate is dissolved in 20 ml 1,4-dioxane and 0.03 mmol (0.14 g) rhenium heptoxide is added thereto. 0.036 mol (2.0 g, 60%) hydrogen peroxide is slowly added dropwise thereto, while stirring. The reaction mixture is subsequently stirred for 16 hours at 90° C., thereafter cooled to 0° C. and mixed with about 20 ml of aqueous saturated sodium sulphite solution. The reaction mixture is extracted with ethyl acetate and the combined organic extracts are evaporated on a rotary evaporator.

The remaining product mixture is subjected to a GC and GC/MS analysis. On the basis of authentic comparison substances, prepared by the epoxidation of methyl 10-undecenoate with peracetic acid or by hydroxylation thereof with performic acid, it is ascertained that, besides unreacted educt, it contains methyl 10,11-dihydroxyundecanoate and methyl 10-epoxyundecenoate. By means of the use of a GC standard (diethyl phthalate), having regard to correction factors previously determined by means of pure substances, the amounts of the reaction products formed are determined quantitatively.

Yield of methyl 10,11-dihydroxyundecanoate 33%, referred to methyl 10-undecenoate.

Yield of methyl 10-epoxyundecenoate 24%, referred to methyl 10-undecenoate.

EXAMPLE 10

Oxidation of 7-tetradecene in glyme (1,2-dimethoxyethane)

0.03 mol (5.9 g) 7-tetradecene is dissolved in 20 ml of glyme (dimethoxyethane) and 0.3 mmol (0.14 g) rhenium heptoxide is added thereto. 0.036 mol (2.0 g, 60%) hydrogen peroxide is slowly added dropwise thereto, while stirring. Subsequently, the reaction mixture is stirred for 16 hours at 90° C., cooled to 0° C. and mixed with about 20 ml of aqueous saturated sodium sulphite solution. A white solid material thereby precipitates out which is separated off by filtration. The yield of tetradecane-7,8-diol is 4.5 g (65% of theory, referred to the olefin).

EXAMPLE 11

Comparison example (corresponds to Example 1 of U.S. Pat. No. 3,518,285)

Oxidation of 1-octene in toluene as solvent with the removal of water by azeotropic distillation.

0.10 mol (11.2 g) 1-octene is dissolved in 40 ml of toluene and 1 mmol (0.48 g) rhenium heptoxide is added thereto. 0.12 mol (6.8 g, 60%) hydrogen peroxide is slowly added dropwise thereto, while stirring. The water formed is continuously removed by means of a water separator over the experimental period of 16 hours.

Subsequently, the reaction mixture is cooled to 0° C. and mixed with about 50 ml of a saturated aqueous solution of sodium sulphite. The solution is extracted several times with diethyl ether and the combined organic extracts are evaporated on a rotary evaporator. The yield of octane-1,2-diol is 4% of theory, referred to the olefin, and the yield of 1-octene oxide is 2% of theory, referred to the olefin.

EXAMPLE 12

Comparison example with the solvents suggested in U.S. Pat. No. 3,518,285; oxidation of 1-octene 0.05 mol (5.6 g) 1-octene is dissolved in the appropriate solvent or, if this is not possible, is suspended therein and 0.5 mmol (0.24 g) rhenium heptoxide is added thereto. 0.06 mol (3.4 g, 60%) hydrogen peroxide is slowly added dropwise thereto, while stirring. After 16 hours at 90° C. or at the boiling point of the appropriate solvent if this is at a lower temperature, the reaction mixture is cooled to 0° C. and mixed with about 30 ml of a saturated aqueous solution of sodium sulphite. The solution is extracted several times with diethyl ether and the combined organic extracts are evaporated on a rotary evaporator.

a) n-hexane as solvent:
  the yield of octane-1,2-diol is 0% of theory, referred to the olefin
  the yield of 1-octene oxide is 0% of theory, referred to the olefin
b) toluene as solvent:
  the yield of octane-1,2-diol is 14% of theory, referred to the olefin
  the yield of 1-octene oxide is 1% of theory, referred to the olefin
c) 1,2-dichloroethane as solvent:
  the yield of octane-1,2-diol is 18% of theory, referred to the olefin
  the yield of 1-octene oxide is 4% of theory, referred to the olefin
d) diethyl carbonate as solvent:
  the yield of octane-1,2-diol is 15% of theory, referred to the olefin
  the yield of 1-octene oxide is 0% of theory, referred to the olefin
e) acetonitrile as solvent:
  the yield of octane-1,2-diol is 6% of theory, referred to the olefin
  the yield of 1-octene oxide is 2% of theory, referred to the olefin.

The superiority of the solvents used according to the present invention in comparison with the solvents used in U.S. Pat. No. 3,518,285 is thus evident.

We claim:

1. Process for the preparation of vicinal diols and/or epoxides by the oxidation of olefinically-unsaturated compounds with the use of an inorganic heptavalent rhenium compound as catalyst and of hydrogen peroxide as oxidation agent, wherein the reaction is carried out under atmospheric conditions and a pH of legs than 3 in a solvent selected from the group consisting of phosphoric acid esters and saturated ethers with a boiling point above 50° C., wherein said group does not include epoxides.

2. Process according to claim 1, wherein the catalyst is used in a concentration of from 0.2 to 5 mol %, referred to an oxidisable carbon-carbon double bond of the olefinically-unsaturated compound.

3. Process according to claim 2, wherein the catalyst is used in a concentration of from 0.8 to 1.2 mol %, referred to an oxidisable carbon-carbon double bond of the olefinically-unsaturated compound.

4. Process according to claim 1, wherein the reaction is carried out at a pH value of from 0 to 2.

5. Process according to claim 1, wherein rhenium heptoxide is used as catalyst.

6. Process according to claim 1, wherein a perrhenate of the general formula M or M'$_2$, in which M is an alkali metal or ammonium and M' is an alkaline earth metal, is used as catalyst.

7. Process according to claim 6, wherein the pH value of the reaction mixture is adjusted to a value of less than 3 by the addition of an inorganic or organic acid which is not oxidisable under the reaction conditions.

8. Process according to claim 7, wherein perchloric acid, phosphoric acid or sulphuric acid is used as inorganic acid and an alkyl or aryl sulphonic acid is used as organic acid.

9. Process according to claim 1, wherein rhenium or a rhenium compound with lower oxidation stage is added to the reaction mixture, the rhenium or rhenium compound thereby being oxidised by hydrogen peroxide to a catalytically-active heptavalent rhenium compound.

10. Process according to claim 9, wherein metallic rhenium or dirhenium decacarbonyl is added.

11. Process according to claim 1, wherein, as solvent, there is used a phosphoric acid trialkyl ester in which each alkyl radical can contain up to 10 carbon atoms.

12. Process according to claim 11, wherein, as solvent, there is used a phosphoric acid trialkyl ester in which each alkyl radical contains 2 to 8 carbon atoms.

13. Process according to claim 12, wherein, as solvent, there is used triethyl phosphate or tri-n-butyl phosphate.

14. Process according to claim 1, wherein, as solvent, there is used a cyclic or acyclic ether with several ether groups.

15. Process according to claim 14, wherein, as solvent, there is used a cyclic or acyclic ether with 2 to 4 ether groups.

16. Process according to claim 15, wherein 1,4-dioxane is used as solvent.

17. Process according to claim 14, wherein glyme or diglyme is used as solvent.

18. Process according to claim 1, wherein the reaction products are separated off from the reaction mixture and the residue is again used as catalyst solution in the reaction.

19. Process according to claim 18, wherein the separation of the reaction products takes place by filtration.

20. Process according to claim 1, wherein, as olefinically-unsaturated compound, there is used a cyclic or acyclic monoolefine, a diolefin or a polyene which can be optionally substituted by one or more functional groups selected from hydroxyl, carboxylic acid, carboxylic acid ester and aryl groups.

21. A process according to claim 1, wherein the hydrogen peroxide is used in a molar ratio of 1:1 to 4:1 to an oxidisable carbon-carbon double bond of the olefinically-unsaturated compound.

22. Process according to claim 21, wherein the hydrogen peroxide is used in a molar ratio of about 1.2:1 to an oxidisable carbon-carbon double bond of the olefinically-unsaturated compound.

23. Process according to claim 1, wherein the reaction is carried out at a temperature of from ambient temperature to 100° C.

24. Process according to claim 23, wherein the reaction is carried out at a temperature of from 70° to 90° C.

* * * * *